US005789435A

United States Patent [19]

Harris et al.

[11] Patent Number: 5,789,435
[45] Date of Patent: Aug. 4, 1998

[54] METHOD TO INCREASE RETINAL AND OPTICAL NERVE HEAD BLOOD FLOW VELOCITY IN ORDER TO PRESERVE SIGHT

[75] Inventors: Alon Harris, Indianapolis, Ind.; William Eric Sponsel, San Antonio, Tex.

[73] Assignee: Advanced Research and Technology Institute, Bloomington, Ind.

[21] Appl. No.: 445,839

[22] Filed: May 22, 1995

[51] Int. Cl.⁶ .................................................. A61K 31/385
[52] U.S. Cl. .................................................. 514/439; 514/912
[58] Field of Search .................................. 514/439, 912

[56] References Cited

U.S. PATENT DOCUMENTS

| | | |
|---|---|---|
| 4,386,098 | 5/1983 | Woltersdorf, Jr. et al. |
| 4,416,890 | 11/1983 | Woltersdorf, Jr. |
| 4,426,388 | 1/1984 | Woltersdorf, Jr. |
| 4,797,413 | 1/1989 | Baldwin et al. |
| 5,153,197 | 10/1992 | Carini et al. |

OTHER PUBLICATIONS

Alon Harris, Abstract, *American Academy of Opthalmology*, "Acute Application of Dorzolamide Increases Retinal and Optic Nerve Head Blood Flow Velocity In Humans" (submitted), 1995.

Wolf et al., Opthalmology, vol. 100, No. 10, (1993), pp. 1561–1566.

Harris et al., Journal of Glaucoma, vol. 5, No. 1 (1996), pp. 39–45.

Harris et al., submitted to Acta Opthal., (1996).

Harris et al., Am. J. Opthal. 118, pp. 642–649, (Nov. 1994).

*Primary Examiner*—Zohreh Fay
*Attorney, Agent, or Firm*—Lowe, Price, LeBlanc & Becker

[57] ABSTRACT

There is disclosed a method for increasing retinal and optic nerve head blood velocity by topical application of carbonic anhydrase inhibitors to the eye.

12 Claims, No Drawings

METHOD TO INCREASE RETINAL AND OPTICAL NERVE HEAD BLOOD FLOW VELOCITY IN ORDER TO PRESERVE SIGHT

BACKGROUND OF THE INVENTION

During most of this century, glaucoma was defined as a blinding eye disease caused by an increased pressure within the eye. This pressure damaged the inner eye tissues leading to the loss of visual field. Science believed that if intraocular pressure (IOP) was lowered to a level under 21 mm on the Mercury Scale, the progression of the disease could be stopped or lessened. However, there are many cases where glaucoma occurs with IOP under 21 mm/Mercury, therefore, the level of IOP is not the major factor in producing this disease. Recent evidence suggests that glaucoma may have a vascular component, possibly vasospastic, as well. New scientific technologies allow us to look more at the back of the eye and evaluate glaucoma from a circulatory, metabolic and hematological angle, therefore, being better able to determine the cause of the disease.

In order to be able to see, light enters through the cornea and the lens; penetrates the back of the eye through the retina; passes the ganglion cells and bipolar cells; then goes down to the outer plexiform layers through the synaptic vesicle, the inner fiber, the nucleus, the outer fibers, the terminal bars, the cilium and finally reaches the photoreceptors which can be considered the instant film processing of the visual light beam. After the light beam has been processed in the photoreceptor disks, it passes back through the cilium, the ellipsoid, myoid, Mueller cells, outer fiber, nucleus, inner fiber, synaptic vesicle, the other plexiform layer, inner nuclear layer, the bipolar cells, the inner plexiform layer, finally reaching the ganglion cells where it is processed into an axon signal. After it reaches the ganglion cells, the signal is transported through the optic nerve fibers to the brain where it is assessed and compounded by the visual brain lobes to form the visual picture. It is believed that the uninterrupted signal carried by the retina, the optic nerve head and the optic nerve fibers is the most crucial aspect to create the visual picture and adequate blood flow which nurtures tissue and therefore assures axon flow. Glaucoma is seen as the progressive loss of optic nerve axons which leads to an interrupted signal flow, therefore, the result is visual field damage which leads over longer periods of time to blindness.

SUMMARY OF THE INVENTION

It has now been found that drugs in the class of carbonic anhydrase inhibitors (CAIs) when administered intraocularly can cause a significant increase in retinal and optic nerve head blood velocity. CAIs include such drugs as dorzolamide, acetazolamide, metazolamide and other compounds which are described in U.S. Pat. Nos. 4,797,413, 4,386,098, 4,416,890 and 4,426,388; and the like. Dorzolamide, S,S-5,6-dihydro-4-ethylamino-6-methyl-4H-thieno-[2,3-b]thiopyran-2-sulfonaimide-7,7 dioxide hydrochloride and its trans enantiomer has recently been approved by the Food and Drug Administration (FDA) for use in the treatment of ocular hypertension associated with glaucoma. CAIs manifest their activity by inhibiting the enzyme, carbonic anhydrase, and impeding their contribution to aqueous humour formation made by the carbonic anhydrase pathway. CAIs block or impede this inflow pathway by inhibiting carbonic anhydrase. Dorzolamide, which has recently been approved under the trademark, TRUSOPT®, is the first topically effective CAI for clinical use.

DETAILED DESCRIPTION OF THE INVENTION

The present invention is directed to a method for increasing retinal and optic nerve head blood velocity by topical application of CAIs to the eye.

The present invention is based upon the discovery that CAIs can preserve or benefit vision by increasing both retinal and optic nerve head blood flow velocity. It was found that the results were attained without any change in retinal vessel width which might have been the expected reason for the increase in flow velocity.

Research was done using Trusopt®, a particular carbonic anhydrase inhibitor. It is a known compound useful as a carbonic anhydrase inhibitor and for the reduction of intraocular pressure as is described in U.S. Pat. No. 4,797,413.

The CAI used is preferably administered in the form of ophthalmic pharmaceutical compositions adapted for topical administration to the eye such as solutions, ointments or as a solid insert. Formulations of this compound may contain from 0.01 to 5% and especially 0.5 to 2% of medicament. Higher dosages as, for example, about 10% or lower dosages can be employed provided the dose is effective in increasing blood flow velocity. For a single dose, from between 0.001 to 5.0 mg, preferably 0.005 to 2.0 mg, and especially 0.005 to 1.0 mg of the compound is applied to the human eye.

The pharmaceutical preparation which contains the compound may be conveniently admixed with a non-toxic pharmaceutical organic carrier, or with a non-toxic pharmaceutical inorganic carrier. Typical of pharmaceutically acceptable carriers are, for example, water, mixtures of water and water-miscible solvents such as lower alkanols or aralkanols, vegetable oils, polyalkylene glycols, petroleum based jelly, ethyl cellulose, ethyl oleate, carboxymethylcellulose, polyvinylpyrrolidone, isopropyl myristate and other conventionally employed acceptable carriers. The pharmaceutical preparation may also contain non-toxic auxiliary substances such as emulsifying, preserving, wetting agents, bodying agents and the like, as for example, polyethylene glycols 200, 300, 400 and 600, carbowaxes 1,000, 1,500, 4,000, 6,000 and 10,000, bacterial components such as quaternary ammonium compounds, phenylmercuric salts known to have cold sterilizing properties and which are non-injurious in use, thimerosal, methyl and propyl paraben, benzyl alcohol, phenyl ethanol, buffering ingredients such as sodium borate, sodium acetates, gluconate buffers, and other conventional ingredients such as sorbitan monolaurate, triethanolamine, oleate, polyoxyethylene sorbitan monopalmitylate, dioctyl sodium sulfosuccinate, monothioglycerol, thiosorbitol, ethylenediamine tetracetic acid, and the like. Additionally, suitable ophthalmic vehicles can be used as carrier media for the present purpose including conventional phosphate buffer vehicle systems, isotonic boric acid vehicles, isotonic sodium chloride vehicles, isotonic sodium borate vehicles and the like. The pharmaceutical preparation may also be in the form of a solid insert. For example, one may use a solid water soluble polymer as the carrier for the medicament. The polymer used to form the insert may be any water soluble non-toxic polymer, for example, cellulose derivatives such as methylcellulose, sodium carboxymethyl cellulose, (hydroxyloweralkyl cellulose), hydroxyethyl cellulose, hydroxypropyl cellulose, hydroxypropylmethyl cellulose; acrylates such as polyacrylic acid salts, ethylacrylates, polyactylamides; natural products such as gelatin, alginates, pectins, tragacanth, karaya, chondrus, agar, acacia; the starch derivatives such as starch acetate, hydroxymethyl starch ethers, hydroxypropyl starch, as well as other synthetic derivatives such as polyvinyl alcohol, polyvinyl pyrrolidone, polyvinyl methyl ether, polyethylene oxide, neutralized carbopol and xanthan gum, and mixtures of said polymer.

Preferably the solid insert is prepared from cellulose derivatives such as methylcellulose, hydroxyethyl cellulose, hydroxypropyl cellulose or hydroxypropylmethyl cellulose or from other synthetic materials such as polyvinyl alcohol, polyvinyl pyrrolidone, polyethylene oxide or polyvinyl methylether. Hydroxypropyl cellulose, one of the preferred polymers for the preparation of the insert is available in several polymeric forms, all of which are suitable in the preparation of these inserts. Thus, the product sold by Hercules, Inc. of Wilmington, Delaware under the name KLUCEL™ such as KLUCEL HF, HWF, MF, GF, JF, LF and EF which are intended for food of pharmaceutical use are particularly useful. The molecular weight of these polymers useful for the purposes described herein may be at least 30,000 to about 1,000,000 or more. Similarly, an ethylene oxide polymer having a molecular weight of up to 5,000,000 or greater, and preferably 100,000 to 5,000,000 can be employed. Further, for example, POLYOX™ a polymer supplied by Union Carbide Co. may be used having a molecular weight of about 50,000 to 5,000,000 or more and preferably 3,000,000 to 4,000,000. Other specific polymers which are useful are polyvinyl pyrrolidine having a molecular weight of from about 10,000 to about 1,000,000 or more, preferably up to about 350,000 and especially about 20,000 to 60,000; polyvinyl alcohol having a molecular weight of from about 30,000 to 1,000,000 or more, particularly about 400,000 and especially from about 100,000 to about 200,000; hydroxypropylmethyl cellulose having a molecular weight of from about 10,000 to 1,000,000 or more, particularly up to about 200,000 and especially about 80,000 to about 125,000; methyl cellulose having a molecular weight of from about 10,000 to about 1,000,000 or more, preferably up to about 200,000 and especially about 50 to 100,000; and CARBOPOL™ (carboxyvinyl polymer) of B. F. Goodrich and Co. designated as grades 934,940 and 941.

It is clear that for the purpose of this invention the type and molecular weight of the polymer is not critical. Any water soluble polymers can be used having an average molecular weight which will afford dissolution of the polymer and accordingly the medicament in any desired length of time. The inserts, therefore, can be prepared to allow for retention and accordingly effectiveness in the eye for any desired period. The insert can be in the form of a square, rectangle, oval, circle, doughnut, semi-circle, ¼ moon shape, and the like. Preferably the insert is in the form of a rod, doughnut, oval or ¼ moon. The insert can be readily prepared, for example, by dissolving the medicament and the polymer in a suitable solvent and the solution evaporated to afford a thin film of the polymer which can then be subdivided to prepare inserts of appropriate size. Alternatively the insert can be prepared by warming the polymer and the medicament and the resulting mixture molded to form a thin film. Preferably, the inserts are prepared by molding or extrusion procedures well known in the art. The molded or extruded product can then be subdivided to afford inserts of suitable size for administration in the eye. The insert can be of any suitable size to readily fit into the eye. For example, castings or compression molded films having a thickness of about 0.25 mm to 15.0 mm can be subdivided to obtain suitable inserts. Rectangular segments of the cast or compressed film having a thickness between about 0.5 and 1.5 mm can be cut to afford shapes such as rectangular plates of 4×5–20 mm or ovals of comparable size. Similarly, extruded rods having a diameter between about 0.5 and 1.5 mm can be cut into suitable sections to provide the desired amount of polymer. For example, rods of 1.0 to 1.5 mm in diameter and about 20 mm long are found to be satisfactory. The inserts may also be directly formed by injection molding. It is preferred that the ophthalmic inserts containing the medicament of the present invention be formed so that they are smooth and do not have any sharp edges or corners which could cause damage to the eye. Since the term smooth and sharp edges or corners are subjective terms, in this application these terms are used to indicate that excessive irritation of the eye will not result from the use of the insert.

The ocular medicinal inserts can also contain plasticizers, buffering agents and preservatives. Plasticizers suitable for this purpose must, of course, also be completely soluble in the lacrimal fluids of the eye. Examples of suitable plasticizers that might be mentioned are water, polyethylene glycol, propylene glycol, glycerine, trimethylol propane, di and tripropylene glycol, hydroxypropyl sucrose and the like. Typically, such plasticizers can be present in the ophthalmic insert in an amount ranging from up to 1 about 30% by weight. A particularly preferred plasticizer is water which is present in amounts of at least about 5% up to about 40%. In actual practice, a water content of from about 10% to about 20% is preferred since it may be easily accomplished and adds the desired softness and pliability to the insert.

When plasticizing the solid medicinal product with water, the product is contacted with air having a relative humidity of at least 40% until said product picks up at least about 5% water and becomes softer and more pliable. In a preferred embodiment, the relative humidity of the air is from about 60% to about 99% and the contacting is continued until the water is present in the product in amounts of from about 10% to about 20%.

Suitable water soluble preservatives which may be employed in the insert are sodium bisulfate, sodium thiosulfate, ascorbate, benzalkonium chloride, chlorobutanol, thimerosal, phenylmercuric acetate, phenylmercuric borate, parabens, benzyl alcohol and phenylethanol. These agents may be present in amounts of from 0.001 to 5% by weight of solid insert, and preferably 0.1 to 2%.

Suitable water soluble buffering agents are alkali, alkali earth carbonates, phosphates, bicarbonates, citrates, borates, and the like, such as sodium phosphate, citrate, borate, acetate, bicarbonate and carbonate. These agents may be present in amounts sufficient to obtain a pH of the system of between 5.5 to 8.0 and especially 7–8; usually up to about 2% by weight of polymer. The insert may contain from about 1 mg to 100 mg of water soluble polymer, more particularly from 5 to 50 mg and especially from 5 to 20 mg. The medicament is present from about 0.1 to about 25% by weight of insert.

The claimed use of the compound to increase retinal and optic nerve head blood flow velocity has been the subject of a study to determine whether Trusopt drops compared to placebo drops had a significant effect on retinal and optic nerve head blood flow velocity in healthy subjects.

In the study, normal, healthy subjects were randomly assigned to receive placebo or 2.0% Trusopt drops to both eyes in a double masked clinical trial. Intraocular pressure and scanning laser video fluorescin angiography were evaluated at baseline and 120 minutes following application. Subjects treated with Trusopt exhibited an accelerated arteriovenous passage time as well as an increase in optic nerve head velocity. Additionally, the expected decrease in intraocular pressure was found.

What is claimed is:

1. A method for maximizing the health of the optic nerve and retina by increasing retinal blood flow velocity and increasing optic nerve head blood velocity which comprises applying to the eye an effective amount of a carbonic anhydrase inhibitor.

2. The method according to claim 1 wherein the carbonic anhydrase inhibitor is applied topically.

3. The method according to claim 2 wherein the carbonic anhydrase inhibitor is selected from the group consisting of dorzolamide, acetazolamide, metazolamide and the like.

4. The method according to claim 3 wherein the carbonic anhydrase inhibitor is dorzolamide.

5. A method for increasing retinal blood flow velocity which comprises applying to the eye an effective amount of a carbonic anhydrase inhibitor.

6. The method according to claim 5 wherein the carbonic anhydrase inhibitor is applied topically.

7. The method according to claim 6 wherein the carbonic anhydrase inhibitor is dorzolamide.

8. A method for increasing optic nerve head blood velocity which comprises applying to the eye an effective amount of a carbonic anhydrase inhibitor.

9. The method according to claim 8 wherein the carbonic anhydrase inhibitor is applied topically.

10. The method according to claim 9 wherein the carbonic anhydrase inhibitor is dorzolamide.

11. The method according to claim 1 wherein the carbonic anhydrase inhibitor is administered as a 0.01 to 5% solution in an opthalmologically acceptable carrier.

12. The method according to claim 11 wherein the carbonic anhydrase inhibitor is administered as a 0.5 to 2% solution in an opthalmologically acceptable carrier.

* * * * *